United States Patent [19]

Takayama et al.

[11] 4,181,732
[45] Jan. 1, 1980

[54] 1-BRANCHED-ALKYLCARBONYL-3-(3,5-DIHALOPHENYL)IMIDAZOLIDINE-2,4-DIONES

[75] Inventors: Chiyozo Takayama, Sonehigashi; Shigeo Yamamoto, Osaka; Toshiro Kato, Hyogo; Yoshio Hisada, Hyogo; Shuichiro Asao, Hyogo; Yoshinori Nakayama, Hyogo, all of Japan

[73] Assignee: Sumitomo Chemical Company, Limited, Osaka, Japan

[21] Appl. No.: 926,396

[22] Filed: Jul. 20, 1978

[30] Foreign Application Priority Data

Aug. 2, 1977 [JP] Japan .................. 52/93182

[51] Int. Cl.$^2$ .................. A61K 31/415; C07D 233/80
[52] U.S. Cl. .................. 424/273 R; 548/312
[58] Field of Search .................. 548/312; 424/273 R

[56] References Cited

U.S. PATENT DOCUMENTS

| | | | |
|---|---|---|---|
| 3,161,652 | 12/1964 | Takamatsu et al. | 548/312 |
| 3,325,361 | 6/1967 | Meunier | 548/312 |
| 3,420,842 | 1/1969 | Lancini et al. | 548/338 |
| 3,668,217 | 6/1972 | Fujinami et al. | 424/273 R |
| 3,716,552 | 2/1973 | Fujinami et al. | 548/312 |
| 4,056,622 | 11/1977 | Takayama et al. | 424/273 R |

FOREIGN PATENT DOCUMENTS

| | | | |
|---|---|---|---|
| 1067822 | 10/1959 | Fed. Rep. of Germany | 548/312 |
| 1167558 | 10/1969 | United Kingdom | 548/312 |

OTHER PUBLICATIONS

Fletcher et al., Nomenclature of Organic Compounds Amer. Chem. Soc., Washington, D.C. 1974, pp. 130–145.

*Primary Examiner*—Alan L. Rotman
*Assistant Examiner*—Natalia Harkaway
*Attorney, Agent, or Firm*—Birch, Stewart, Kolasch andBirch

[57] ABSTRACT

1-Branched-alkylcarbonyl-3-(3,5-dihalophenyl)imidazolidine-2,4-diones of the formula:

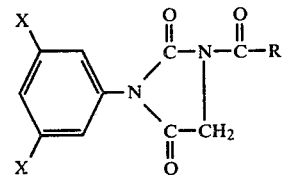

wherein X is a chlorine or bromine atom and R is a $C_3$–$C_5$ branched alkyl group, which show high fungicidal activities without any material toxicity to mammals and plants and which can be produced by reacting the corresponding 1-unsubstituted compound with a branched alkanecarboxylic acid or a reactive derivative thereof.

8 Claims, No Drawings

1-BRANCHED-ALKYLCARBONYL-3-(3,5-DIHALOPHENYL)IMIDAZOLIDINE-2,4-DIONES

The present invention relates to 1-branched-alkylcarbonyl-3-(3,5-dihalophenyl)imidazolidine-2,4-diones (hereinafter referred to as "1-branched-alkylcarbonylimidazolidinedione(s) [I]") of the formula:

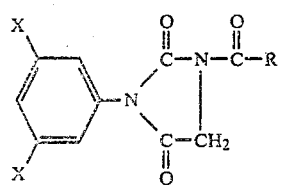

wherein X is a chlorine or bromine atom and R is a $C_3$-$C_5$ branched alkyl group (e.g. isopropyl, sec-butyl, isobutyl, tert-butyl, 2-methylbutyl, 1-ethylpropyl, 1-methylbutyl, neo-pentyl, isopentyl), and their production and use.

It is already well known that some of the 3-(3,5-dihalophenyl)imidazolidine-2,4-dione derivatives, of which the 1- and 5-positions may be optionally substituted with various substituents, have a fungicidal activity against certain microorganisms (U.S. Pat. Nos. 3,668,217 and 3,716,552). As the results of an extensive study, it has now been found that the said compounds [I] having a branched alkylcarbonyl group at the 1-position exhibit a fungicidal activity which is widely applicable and markedly superior as compared with their homologues, and in addition show no material phytotoxicity to plants and low mammalian toxicity.

The foregoing compounds, 1-branched-alkylcarbonylimidazolidinediones [I], are especially effective in controlling the diseases of agricultural and horticultural crops caused by the phytopathogenic fungi belonging to Alternaria genus, such as black spot of pear (*Alternaria kikuchiana*), Alternaria leaf spot of apple (*Alternaria mali*), early blight of tomato (*Alternaria solani*), early blight of potato (*Alternaria solani*), black spot of sweet potato (*Alternaria bataticola*), gray leaf spot of rape (*Alternaria brassicae*), brown spot of tobacco (*Alternaria longipes*), Alternaria sooty spot of chinese cabbage (*Alternaria brassicicola*), Alternaria leaf spot of chinese cabbage (*Alternaria herculea*), Alternaria leaf spot of Japanese radish (*Alternaria japonica*), leaf blight of carrot (*Alternaria carotae*), Alternaria leaf spot of onion (*Alternaria porri*) and Alternaria blight of cucumber (*Alternaria cucumerina*). In addition to the said diseases, several plant diseases which cause serious damages in agriculture and horticulture can be effectively controlled by the application of the 1-branched-alkylcarbonylimidazolidinediones [I]. Those diseases include brown rot of peach (*Sclerotinia cinerea*), melanose of citrus (*Diaporthe citri*), common green mold of citrus fruits (*Penicillium digitatum*), blue mold of citrus fruits (*Penicillium italicum*), gray mold of grape (*Botrytis cinerea*), gray mold and Sclerotinia rot of beans and vegetables (*Botrytis cinerea* and *Sclerotinia sclerotiorum*) and the like.

Recently, the emergence of plant pathogens resistant to fungicides has been often noticed in fields, becoming a serious practical problem in crop protection with fungicide application. Then, the 1-branched-alkylcarbonylimidazolidinediones [I] have been found to exhibit a strong fungitoxicity towards those fungicide-resistant pathogens. For example, they have the same fungitoxic activity on the Polyoxin-resistant strain of *Alternaria kikuchiana* as on the respective wild strains (susceptible strains). It can be therefore expected that the 1-branched-alkylcarbonylimidazolidinediones [I] exert a prominent controlling effectiveness on plant diseases in the fields where fungicide-resistant pathogens have already emerged.

Furthermore, the 1-branched-alkylcarbonylimidazolidinediones [I] possess a systemic property in plants. The compounds can penetrate from leaf surfaces into leaf tissues and be absorbed by roots and translocated to leaves. Due to this property, the compounds can effectively suppress propagation of the pathogens invading leaf tissues, in addition to protecting plants from infection.

The 1-branched-alkylcarbonylimidazolidinediones [I] of the present invention structurally relate to some of the compounds disclosed in U.S. Pat. No. 3,716,552, but their effectiveness in controlling the said diseases are superior to those of the latter compounds, and the 1-branched-alkylcarbonylimidazolidinediones [I] are still effective with the application at lower dosages. This indicates that substitution with a branched alkylcarbonyl group at the 1-position of 3-(3,5-dihalophenyl)imidazolidine-2,4-dione derivatives results in marked increase in their fungitoxic activities. The present inventors are the first to point out this unexpected increase of activity.

A main object of the present invention is to provie novel 1-branched-alkylcarbonylimidazolidinediones [I], which are useful as fungicides. Another object of this invention is to provide a process for producing such 1-branched-alkylcarbonylimidazolidinediones [I]. A further object of the invention is to provide fungicidal compositions containing such 1-branched-alkylcarbonylimidazolidinediones [I]. These and other objects and advantages of the invention will become apparent from the foregoing and subsequent descriptions.

The 1-branched-alkylcarbonylimidazolidinediones [I] can be produced by reacting the corresponding 1-unsubstituted compound of the formula:

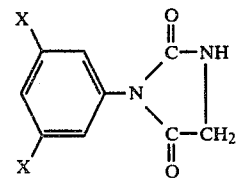

wherein X is as defined above, with a branched alkanecarboxylic acid of the formula:

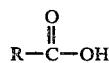

wherein R is as defined above or a reactive derivative thereof. Usually, the reaction is effected between the said 1-unsubstituted compound [II] and a branched alkanecarbonyl halide of the formula:

wherein R is as defined above and Y is a halogen atom or a branched alkanecarboxylic anhydride of the formula:

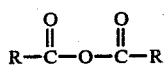 [V]

wherein R is as defined above.

Examples of typical procedures for carrying out the said production so as to obtain the objective 1-branched-alkylcarbonylimidazolidinediones [I] in a good yield are as follows:

Procedure A

The starting 1-unsubstituted compound [II] is reacted with an equivalent or excessive molar amount of the branched alkanecarbonyl halide [IV] at room temperature (0°-35° C.) in the presence or absence of a suitable solvent (e.g. tetrahydrofuran, methyl isobutyl ketone, benzene, toluene, xylene, chlorobenzene, chloroform, carbon tetrachloride, nitrobenzene) and, if necessary, in the presence of a dehydrohalogenating agent (e.g. triethylamine, N-methylmorpholine, pyridine, dimethylaniline, diethylaniline) and/or with heating (up to reflux) to give the 1-branched-alkylcarbonylimidazolidinedione [I].

Procedure B

The starting 1-unsubstituted compound [II] is reacted with an equivalent or excessive molar amount of the branched alkanecarboxylic anhydride [V] at room temperature (0°-35° C.) in the presence or absence of a suitable solvent (e.g. chloroform, carbon tetrachloride, benzene, toluene, xylene, ligroin) and, if necessary, with heating to give the 1-branched-alkylcarbonylimidazolidinedione [I].

The 1-branched-alkylcarbonylimidazolidinedione [I] thus produced may be purified, if necessary, by a per se conventional procedure such as recrystallization from a proper solvent.

The starting 1-unsubstituted compound [II]0 is obtainable, for instance, by the process as described in U.S. Pat. No. 3,668,217.

In actual application as fungicides, the 1-branched-alkylcarbonylimidazolidinediones [I] may be used alone without incorporation of other ingredients such as carriers and diluents or, for easier application, in admixture with such solid carriers or diluents as talc, clay and the like or with such liquid carriers or diluents as organic solvents and the like. The fungicidal compositions can be formulated into any of the ordinarily adopted forms such as, for example, dusts, wettable powders, oil sprays, aerosols, tablets, emulsifiable concentrates and granules.

The foregoing compositions generally contain 0.1 to 95.0% by weight, preferably 0.2 to 90.0% by weight of the active ingredient (including other ingredients mixed therewith). A suitable amount of the compositions applied in practice is generally 10 to 1000 g/10 are, and the concentration of the compositions applied is preferably within the range of 0.001 to 0.1 % by weight. Since, however, the amount and concentration depend upon the composition forms, application times, application methods, application sites, diseases and crops, they may be properly increased or decreased irrespective of the aforesaid ranges.

Further, the 1-branched-alkylcarbonylimidazolidinediones [I] may be used in admixture with other fungicides such as, for example N-(3,5-dichlorophenyl)-1,2-dimethylcyclopropane-1,2-dicarboximide, S-n-butyl-S'-p-tert-butylbenzyl-N-3-pyridyldithiocarbonimidate, O,O-dimethyl-O-2,6-dichloro-4-methylphenylphosphorothioate, methyl N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(dimethylthiocarbamoyl)-disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazol-1yl)-2-butanone, 1,2-bis(3-methoxycarbonyl-2-thioureido)benzene and the like; and the 1-branched-alkylcarbonylimidazolidinediones [I] may be used in admixture with insecticides such as, for example, O,O-dimethyl-O-(4-nitro-m-tolyl)phosphorothioate, O-p-cyanophenyl-O,O-dimethylphosphorothioate, O-p-cyanophenyl-O-ethylphenylphosphonothioate, O,O-dimethyl-S-(N-methylcarbamoylmethyl)phosphorodithioate, 2-methoxy-4H-1,3,2-benzodioxaphosphorine-2-sulfide, O,O-dimethyl-S'-(1-ethoxycarbonyl-1-phenylmethyl)phosphorodithioate, α-cyano-3-phenoxybenzyl-2-(4-chlorophenyl)isovalerate, 3-phenoxybenzyl-2,2-dimethyl-3-(2,2-dichlorovinyl)cyclopropanecarboxylate, 3-phenoxybenzyl chrysanthemate and the like; and, in every case, the controlling effects of the individual chemicals are not decreased. Accordingly, simultaneous control of two or more pests and injurious insects is possible. In addition thereto, they may be used in admixture with such agricultural chemicals as nematocides and acaricides and with fertilizers.

Practical and presently preferred embodiments of the present invention are illustratively shown in the following examples, wherein parts and % are by weight.

EXAMPLE 1

Production of the 1-branched-alkylcarbonylimidazolidinediones [I]:

Procedure A 0.05 mole of a 3-(3,5-dihalophenyl)imidazolidine-2,4-dione derivative of the formula [II] and 0.66 mole of triethylamine are dissolved in 150 ml of toluene, and 0.06 mole of an acid chloride of the formula [IV] is added thereto dropwise slowly at room temperature with stirring. After the addition is finished, the mixture is heated under reflux for 7 hours. After the reaction is finished, the reaction mixture is filtered, and the filtrate is washed with dilute hydrochloric acid, sodium bicarbonate-saturated water and water. After washing, the toluene layer is dried over anhydrous sodium sulfate and concentrated under reduced pressure to obtain the objective 1-branched-alkylcarbonyl-3-(3,5-dihalophenyl)imidazolidine-2,4-dione derivative of the formula [I] in a high yield. The crude product is recrystallized from ethanol or purified by column chromatography (stationary phase, silica gel; developer, chloroform) to obtain a pure product.

Procedure B 0.05 mole of a 3-(3,5-dihalophenyl)imidazolidine-2,4-dione derivative of the formula [II] and 0.15 mole of an acid anhydride of the formula [V] are dissolved in 50 ml of toluene. The mixture is heated under reflux for 15 hours. After the reaction is finished, the reaction solution is cooled to room temperature and poured into sodium bicarbonate-saturated water, followed by stirring for some time. The solid material obtained is collected by filtration, washed with water several times and dried to obtain the objective 1-branched-alkylcarbonyl-3-(3,5-dihalophenyl)imidazolidine-2,4-dione derivative of the formula [I] in a high yield. The crude product is recrystallized from ethanol to obtain a pure product.

According to either one of the above procedures, the 1-branched-alkylcarbonylimidazolidinediones [I] as shown in Table 1 are prepared.

Table 1

| | Starting materials | | 1-Branched-alkylcarbonyl-3-(3,5-dihalophenyl)imidazolidinedione compound [I] | | | | | | | |
|---|---|---|---|---|---|---|---|---|---|---|
| Procedure | 3-(3,5-Dihalo-phenyl)imida-zolidine-2,4-dione compound [II] | Acid halide [IV] or acid anhydride [V] | Compound No. | Chemical structure | Physical constant | Yield (%) | \multicolumn{4}{c}{Elementary analysis (%)} |
| | | | | | | | C | H | N | Halogen |
| B | [3,5-diCl-phenyl imidazolidine-2,4-dione] | isobutyric anhydride | 1 | [1-isobutyryl-3-(3,5-dichlorophenyl)imidazolidinedione] | M.P., 97.0°–99.0° C. | 91 | 49.54 (49.47) | 3.84 (3.97) | 8.89 (8.91) | (Cl) 22.50 (22.79) |
| B | [3,5-diCl-phenyl imidazolidine-2,4-dione] | 2-methylbutyric anhydride | 2 | [1-(2-methylbutyryl)-3-(3,5-dichlorophenyl)imidazolidinedione] | M.P., 92.0°–93.0° C. | 82 | 51.08 (51.01) | 4.29 (4.35) | 8.51 (8.62) | (Cl) 21.54 (21.69) |
| A | [3,5-diCl-phenyl imidazolidine-2,4-dione] | pivaloyl chloride | 3 | [1-pivaloyl-3-(3,5-dichlorophenyl)imidazolidinedione] | M.P., 138.5°–140.0° C. | 87 | 51.08 (50.94) | 4.29 (4.18) | 8.51 (8.63) | (Cl) 21.54 (21.66) |
| A | [3,5-diCl-phenyl imidazolidine-2,4-dione] | 3,3-dimethylbutyryl chloride | 4 | [1-(3,3-dimethylbutyryl)-3-(3,5-dichlorophenyl)imidazolidinedione] | $n_D^{25}$, 1.5460 | 90 | 52.49 (52.54) | 4.70 (4.87) | 8.16 (7.93) | (Cl) 20.66 (21.01) |
| A | [3,5-diBr-phenyl imidazolidine-2,4-dione] | 2-methylbutyryl chloride | 5 | [1-(2-methylbutyryl)-3-(3,5-dibromophenyl)imidazolidinedione] | $n_D^{26}$, 1.5471 | 80 | 40.22 (39.99) | 3.38 (3.21) | 6.70 (6.48) | (Br) 38.22 (38.60) |

Table 1-continued

| | Starting materials | | | 1-Branched-alkylcarbonyl-3-(3,5-dihalophenyl)imidazolidinedione compound [I] | | | | | | | |
|---|---|---|---|---|---|---|---|---|---|---|---|
| Procedure | 3-(3,5-Dihalo-phenyl)imida-zolidine-2,4-dione compound [III] | Acid halide [IV] or acid anhydride [V] | Compound No. | Chemical structure | Physical constant | Yield (%) | Elementary analysis (%) | | | | |
| | | | | | | | C | H | N | Halogen | |
| A | [3-(3,5-dichlorophenyl)imidazolidine-2,4-dione] | CH$_3$CH$_2$CH(CH$_3$)—C(O)—Cl | 6 | [1-(2-methylbutyryl)-3-(3,5-dichlorophenyl)imidazolidine-2,4-dione] | M.P., 78.5°–79.5° C. | 77 | 51.08 (51.15) | 4.29 (4.31) | 8.51 (8.53) | (Cl) 21.54 (21.79) | |
| A | [3-(3,5-dichlorophenyl)imidazolidine-2,4-dione] | CH$_3$CH$_2$CH$_2$CH(CH$_3$)—C(O)—Cl | 7 | structure with —N—C(O)—CH$_2$CH(CH$_3$)CH$_2$CH$_3$ | M.P., 65.0°–66.0° C. | 89 | 52.49 (52.72) | 4.70 (4.69) | 8.16 (8.39) | (Cl) 20.66 (20.60) | |
| A | [3-(3,5-dichlorophenyl)imidazolidine-2,4-dione] | CH$_3$CH$_2$CH(CH$_2$CH$_3$)—C(O)—Cl | 8 | structure with —N—C(O)—CH(CH$_2$CH$_3$)CH$_2$CH$_3$ | M.P., 64.0°–65.0° C. | 80 | 52.49 (52.56) | 4.70 (4.70) | 8.16 (8.35) | (Cl) 20.66 (20.87) | |
| A | [3-(3,5-dichlorophenyl)imidazolidine-2,4-dione] | CH$_3$CH$_2$CH$_2$CH$_2$CH(CH$_3$)—C(O)—Cl | 9 | structure with —N—C(O)—CH(CH$_3$)CH$_2$CH$_2$CH$_3$ | M.P., 104.0°–105.0° C. | 86 | 52.49 (52.36) | 4.70 (4.50) | 8.16 (8.16) | (Cl) 20.66 (20.85) | |
| A | [3-(3,5-dichlorophenyl)imidazolidine-2,4-dione] | CH$_3$CHCH$_2$CH$_2$—C(O)—Cl with CH$_3$ branch | 10 | structure with —N—C(O)—CH$_2$CH$_2$CH(CH$_3$)CH$_3$ | M.P., 82.5°–83.5° C. | 74 | 52.49 (52.36) | 4.70 (4.73) | 8.16 (8.17) | (Cl) 20.66 (20.71) | |

Note:
In the elemental analysis, the values as calculated are unparenthesized and the values as found are parenthesized.

EXAMPLE 2

Formulation of compositions:

(a) Dust 0.2 Part of the compound (2) and 99.8 parts of clay were thoroughly pulverized and mixed together to obtain a dust containing 0.2% of the active ingredient. In application, the dust was dusted as such.

(b) Dust

3 Parts of the compound (8) and 97 parts of talc were thoroughly pulverized and mixed together to obtain a dust containing 3% of the active ingredient. In application, the dust was dusted as such.

(c) Wettable powder

50 Parts of the compound (2), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

(d) Wettable powder

90 Parts of the compound (9), 5 parts of a wetting agent of the alkylbenzenesulfonate type and 5 parts of diatomaceous earth were thoroughly pulverized and mixed together to obtain a wettable powder containing 90% of the active ingredient. In application, the wettable powder was diluted with water, and the resulting solution was sprayed.

(e) Emulsifiable concentrate

10 Parts of the compound (4), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

(f) Granule

5 Parts of the compound (3), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the 1-branched-alkyl-carbonylimidazolidinediones [I]. In these examples, the compound numbers correspond to those in Table 1.

EXAMPLE 3

Fungicidal activity test on fungicide-resistant pathogens:

Ten milliliters of a potato sucrose agar medium were turned into a solution by heating, and each of the emulsifiable concentrates containing the test compounds was added to the solution and well mixed. The mixture was flowed into a glass Petri dish of 9 cm in diameter to make an agar plate. After the agar was hardened, mycelial discs (5 mm in diameter) of a fungicide-resistant strain of black spot fungus (*Alternaria kikuchiana*) resistant to Polyoxin which was isolated from pears and a wild (susceptible) strain of *Alternaria kikuchiana* were each placed at the center of the agar plate and incubated at 27° C. for 4 days. After the incubation, the diameter of the grown colony was measured, and the percentage of growth inhibition was calculated from the following equation in comparison with an untreated plot:

$$\text{Percentage of growth inhibition (\%)} = 100 - \frac{\text{Diameter of colony in treated plot}}{\text{Diameter of colony in untreated plot}} \times 100$$

As the result, the compounds of the present invention showed a strong antifungal activity on a fungicide-resistant strain of *Alternaria kikuchiana* as well as on a susceptible wild strain of *Alternaria kikuchiana*, as shown in Table 2.

Table 2

Fungicidal effect on *Alternaria kikuchiana*:

| Compound No. | Concentration of active ingredient (ppm) | Percentage of growth inhibition (%) Fungicide-resistant strain | Percentage of growth inhibition (%) Wild susceptible strain |
|---|---|---|---|
| 2 | 10 | 95 | 96 |
|   | 1  | 76 | 78 |
| 4 | 10 | 93 | 92 |
|   | 1  | 61 | 64 |
|   | 10 | 69 | 68 |
|   | 1  | 45 | 49 |
| Polyoxin*² | 100 | 4 | 60 |
|   | 10 | 0 | 48 |
|   | 1  | 0 | 16 |

Note:
*¹Compound disclosed in U.S. Pat. No. 3,716,552.
*²Commercially available fungicide; Polyoxin complex consisting essentially of Polyoxin B.

EXAMPLE 4

Protective activity test on black spot of pear (*Alternaria kikuchiana*):

A 3-year old tree of pear (var.: 20-Seiki) cultivated in a flower pot of 30 cm in diameter was used as a test plant. Each of the emulsifiable concentrates containing the test compounds was diluted with water to a required concentration. When each plant shot out three to four young branches having 10 to 20 leaves thereon, the prepared aqueous solution was sprayed thereon in a rate of 30 ml/seedling. The plant was cultivated in a green-house for 7 days after spraying. The whole body of the plant was then inoculated by spraying the spore suspension of *Alternaria kikuchiana* cultured in a vegetable juice agar medium for 10 days. The plant was then placed in a humid chamber for 24 hours after inoculation and then in a green-house for 2 days. The disease severity was examined as follows using a disease index (0, 1, 2, 3, 4, 5):

| Disease severity | Disease index |
|---|---|
| No infected area | 0 |
| Infected leaf area of less than 10% | 1 |
| Infected leaf area of 10 to less than 20% | 2 |
| Infected leaf area of 20 to less than 40% | 3 |
| Infected leaf area of 40 to less than 60% | 4 |
| Infected leaf area of 60 | 5 |

-continued

| Disease severity | Disease index |
|---|---|
| % or more | |

The disease severity was calculated according to the following equation:

$$\text{Disease severity (\%)} = \frac{\Sigma(\text{Disease index}) \times (\text{Number of leaves})}{5 \times (\text{Total number of leaves examined})} \times 100$$

As a result, the compounds of the present invention were much superior in the protective activity to the control compounds tested at the same time, as shown in Table 3.

Table 3

| Compound No. | Concentration of active ingredient (ppm) | Disease severity (%) |
|---|---|---|
| 1 | 500 | 4.3 |
| 2 | 500 | 3.0 |
| 3 | 500 | 7.4 |
| 4 | 500 | 8.9 |
| 5 | 500 | 2.6 |
| 6 | 500 | 5.5 |
| 7 | 500 | 3.7 |
| 8 | 500 | 4.0 |
| 9 | 500 | 2.1 |
| 10 | 500 | 9.8 |
| [structure] *1 | 500 | 31.6 |
| [structure] *2 | 500 | 24.2 |
| No treatment | — | 77.8 |

Note:
*1 Compound disclosed in U.S. Pat. No. 3,716,552.
*2 Commercially available fungicide; generic name "Captafol".

EXAMPLE 5

Protective activity test on Alternaria leaf spot of apple (*Alternaria mali*):

A 3-year old seedling of apple (var.: Indo) cultivated in a flower pot of 30 cm in diameter was used as a test plant. Each of the emulsifiable concentrates of the test compounds was diluted with water to a required concentration. When each seedling shot out three to four young branches having 10 to 20 young leaves thereon, the prepared aqueous solution was sprayed thereon in a rate of 30 ml per seedling. After the spraying, the seedling was cultivated in a green-house for 6 days. The whole body of the seedling was then inoculated by spraying the spore suspension of *Alternaria mali*. The seedling was then placed in a humid chamber for 24 hours and then in a green-house for 2 days. The infectious state was then examined. The degree of infection was examined by the following method: the leaves examined were measured for a percentage of infected area and classified into the corresponding disease indices, 0, 1, 2, 3, 4, 5; the leaves belonging to the same disease indices were summed up, $n_0$, $n_1$, $n_2$, $n_3$, $n_4$, $n_5$; and the disease severity was calculated according to the following equation.

| Disease index | Percentage of infected area |
|---|---|
| 0 | No infection |
| 1 | Infected area of less than 10% |
| 2 | Infected area of 10 to less than 20% |
| 3 | Infected area of 20 to less than 40% |
| 4 | Infected area of 40 to less than 60% |
| 5 | Infected area of 60% or more |

$$\text{Disease severity (\%)} = \frac{0 \times n_0 + 1 \times n_1 + \ldots + 5 \times n_5}{5 \times n} \times 100$$

The results of this test are shown in Table 4. As is apparent from the test results, the compounds of the present invention show a higher protective activity than the control compound.

Table 4

| Compound No. | Concentration of active ingredient (ppm) | Disease severity (%) |
|---|---|---|
| 1 | 500 | 7.2 |
| 2 | 500 | 2.4 |
| 3 | 500 | 9.6 |
| 4 | 500 | 5.7 |
| 5 | 500 | 3.0 |
| 6 | 500 | 8.1 |
| 7 | 500 | 4.1 |
| 8 | 500 | 3.6 |
| 9 | 500 | 1.7 |
| 10 | 500 | 9.9 |
| [structure] *1 | 500 | 36.8 |
| [structure] *2 | 500 | 27.1 |
| No treatment | — | 79.6 |

Note:
*1 Compound disclosed in U.S. Pat. No. 3,716,552.
*2 Commercially available fungicide; generic name "Captafol".

EXAMPLE 6

Protective activity test on blue mold of orange (*Penicillium italicum*):

Orange fruits (var.: Unshū) were well washed with water and air-dried. Each of the emulsifiable concentrates containing the test compounds was diluted with water to a required concentration and the air-dried orange fruits were dipped in the aqueous solution for 1 minute. After air-drying, the surface of the fruit was inoculated by spraying a spore suspension of *Pencillium italicum* cultured in a potato agar medium for 5 days. After the fruits were placed in a humid chamber for 7 days after inoculation, the disease severity was examined using a disease index (0, 1, 2, 3, 4, 5). The results are shown in the mean value of disease index.

| Disease severity | Disease index |
| --- | --- |
| No infected area | 0 |
| Infected surface area of less than 20% | 1 |
| Infected surface area of 20 to less than 40% | 2 |
| Infected surface area of 40 to less than 60% | 3 |
| Infected surface area of 60 to less than 80% | 4 |
| Infected surface area of 80% or more | 5 |

As the result, the compounds of the present invention were superior in the protective activity to the control compounds tested at the same time, as shown in Table 5.

Table 5

| Compound No. | Concentration of active ingredient (ppm) | Mean value of disease index |
| --- | --- | --- |
| 1 | 100 | 0.5 |
| 2 | 100 | 0.0 |
| 3 | 100 | 0.2 |
| 4 | 100 | 0.4 |
| 5 | 100 | 0.1 |
| 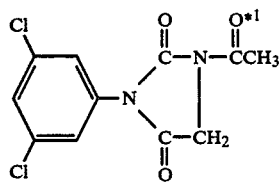 | 200 | 2.8 |

Table 5-continued

| Compound No. | Concentration of active ingredient (ppm) | Mean value of disease index |
| --- | --- | --- |
| 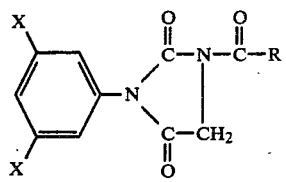 | 200 | 3.0 |
| No treatment | — | 5.0 |

Note:
*1 & *2 Compounds disclosed in U.S. Pat. No. 3,716,552.

What is claimed is:
1. A compound of the formula:

wherein X is a chlorine or bromine atom and R is a $C_3$–$C_5$ branched alkyl group.

2. The compound according to claim 1, wherein X is a chlorine or bromine atom and R is an isopropyl, sec-butyl, isobutyl, tert-butyl, 2-methylbutyl, 1-ethylpropyl, 1-methylbutyl, neopentyl or isopentyl group.

3. The compound according to claim 1, wherein X is a chlorine atom and R is an isobutyl group.

4. The compound according to claim 1, wherein X is a chlorine atom and R is a tert-butyl group.

5. The compound according to claim 1, wherein X is a chlorine atom and R is a 1-ethylpropyl group.

6. A fungicidal composition which comprises as an active ingredient a fungicidally effective amount of the compound according to claim 1 and an inert carrier.

7. A method for controlling fungi which comprises applying a fungicidally effective amount of the compound according to claim 1 to the fungi.

8. The method according to claim 7, wherein the fungi belong to the genus Alternaria.